(12) United States Patent
Schaff et al.

(10) Patent No.: US 12,342,812 B2
(45) Date of Patent: Jul. 1, 2025

(54) ACTIVE BIOLOGICAL SAMPLE PROCESSING AND THERMAL MANAGEMENT DEVICES

(71) Applicant: LABORATORY CORPORATION OF AMERICA HOLDINGS, Burlington, NC (US)

(72) Inventors: Ulrich Schaff, Livermore, CA (US); Angela Le, San Jose, CA (US); Tifany Pan, Walnut Creek, CA (US); Kyungjin Hong, Livermore, CA (US); Clara Neal, Livermore, CA (US)

(73) Assignee: LABORATORY CORPORATION OF AMERICA HOLDINGS, Burlington, NC (US)

( * ) Notice: Subject to any disclaimer, the term of this patent is extended or adjusted under 35 U.S.C. 154(b) by 856 days.

(21) Appl. No.: 17/385,155

(22) Filed: Jul. 26, 2021

(65) Prior Publication Data
US 2022/0022449 A1 Jan. 27, 2022

Related U.S. Application Data

(60) Provisional application No. 63/056,909, filed on Jul. 27, 2020.

(51) Int. Cl.
| | |
|---|---|
| *A01N 1/148* | (2025.01) |
| *A01N 1/145* | (2025.01) |
| *B04B 5/04* | (2006.01) |
| *B04B 9/02* | (2006.01) |
| *B04B 9/10* | (2006.01) |
| *B04B 15/02* | (2006.01) |
| *G01N 1/40* | (2006.01) |

(52) U.S. Cl.
CPC ............. *A01N 1/148* (2025.01); *A01N 1/145* (2025.01); *B04B 5/0414* (2013.01); *B04B 9/02* (2013.01); *B04B 9/10* (2013.01); *B04B 15/02* (2013.01); *G01N 1/4077* (2013.01)

(58) Field of Classification Search
CPC ...................................................... A01N 1/148
See application file for complete search history.

(56) References Cited

U.S. PATENT DOCUMENTS

2019/0015827 A1* 1/2019 Berthier ................. B65D 59/04

* cited by examiner

*Primary Examiner* — Rosanne Kosson
(74) *Attorney, Agent, or Firm* — Kilpatrick Townsend & Stockton LLP

(57) ABSTRACT

Embodiments for a portable and compact centrifugation and thermal management system capable of separating and transporting biological samples while maintaining sample quality for periods of shipment time are described. A compact, automatic centrifuge holding exactly one sample tube is inside an insulating and thermally managed container suitable for standard shipping. A rotor to retain a sample tube is pre-balanced. An electronic controller starts, times and stops centrifugation automatically, responsive to placement of a lid. Thermal management may comprise a phase change material. Embodiments are free of user controls. Embodiments are free of the need for external power or external control.

13 Claims, 3 Drawing Sheets

Cross-section view

Cross-section view

Top view

Side view

B-B' cross-section

ACTIVE BIOLOGICAL SAMPLE PROCESSING AND THERMAL MANAGEMENT DEVICES

BACKGROUND OF THE INVENTION

This invention relates to processing and transport of biological specimens. One such biological specimen is whole blood, which may be processed by separation into plasma and cellular components. Processing and transport may be conducted in order to enable laboratory analysis such as diagnostic testing.

Diagnostic testing may be conducted on biological samples such as blood and serum may. For diagnostic purposes, blood and serum may require a temperature range under which the fluids maintain their quality for diagnostic applications for a period of time. For example, serum may be stored at a temperature range of eight to 32° C. for a period of time of up to 48 hours. Alternately, serum may be stored at a temperature range of four to eight ° C. for a period of time of up to seven days. Alternately, serum may be frozen at a temperature range of −20° C. or lower for a period of time of up to one month. Whole blood may be stored at four to eight ° C., but only for 24 hours, and it cannot be frozen. Different samples may be kept at different temperature ranges, when used for different types of analysis. When a temperature range is not maintained, the sample's composition may change, particularly the composition of the liquid fraction may change thus giving inaccurate test results. Temperatures that are too low may generally result in damage to enveloped materials such as cells due to formations of intracellular ice, or may result in the formation of particulate matter due to aggregation of proteins and other dissolved substances. Elevated temperatures tend to accelerate degradation of proteins and enveloped materials such as cells due to faster chemical reactions at higher temperatures. Therefore, it is critical to implement a temperature regulation method to ensure that the sample composition remains stable when biological samples are to be shipped.

Current thermal regulation methods for shipping can be impractical for certain users, as they require multiple of packaging and imposition of thermal moderators such as packs of frozen material. It is also difficult ensure the samples will be kept in ideal temperatures during the shipping process regardless of the external conditions during shipping such as hot or alternately freezing weather. Passive cooling approaches used alone may not allow for definite temperature control, as temperatures can fluctuate wildly in shipping vehicles. The cargo areas in the back of trucks can rise up to 60° C., causing similar shifts in temperature in packages contained within. In these cases, phase change material (PCM) such as water/ice, hydrated salts, paraffin waxes, and biological oils may be used to provide cooling or heating energy by the release or absorption of the thermal heat of fusion as appropriate in the vicinity of the temperature of the melting point of the PCM. Phase change materials may provide a thermal reserve against temperature change greater than passive materials relying solely on the thermal heat capacity, However, phase change materials may require active refrigeration or heating to achieve the desired phase state at the initial condition. For instance, a typical cold pack may require freezing by conventional refrigeration prior to its use in thermal regulation of packaged materials. Active refrigeration such as by Carnot cycle evaporation and condensation of a coolant, direct evaporative cooling, endothermic reactions, or thermoelectric cooling may also be used to provide active thermal regulation to samples in shipping.

Prior art active coolant-cycle mediated refrigeration of shipped packages is typically conducted at the level of entire shipping containers such as a truck or shipping container. Such prior art cooling is expensive and may not cover the initial and final portions of a shipment, such as within a building or campus, or during inspection.

Typical cold chain processing and shipment of a blood specimens require use of a centrifuge and refrigerated ice packs. Such equipment and skills are not available at many potential sites of blood draw due to power requirement, space, untrained users, and time.

Prior art unpowered centrifuges, such as hand-crank operated spinners, do not provide the consistent spin rate and spin time performance required by regulations and standards for diagnostic testing. Prior art devices and their elements are generally single-use and not re-usable. Prior art devices and their elements are generally not sterilizable.

SUMMARY OF THE INVENTION

Embodiments enable remote blood separation. Without requiring an external power source, use in remote environments or emergency vehicles may be achieved. Although unpowered centrifuges, such as hand-crank operated spinners, exist, a powered centrifuge such as versions described herein provide the consistent spin rate and spin time performance required by regulations and standards for diagnostic testing, Further, balancing and operating a prior art conventional centrifuge is not within the capability of most untrained users, such as is common in remote, home, or mobile environments. At-home or remote testing is facilitated by a small, portable, battery-powered centrifuge such as described herein. Preferred embodiments have a minimal size to facilitate portability, fitting within a typical pocket, backpack, or purse. Emerging devices for higher capillary blood draw to obtain larger blood samples, such as the Tasso On Demand product (Tasso, Inc, Seattle, Wash.), which collects blood through a patch rather than a needle, may be available to users at home. Personal use by a user or patient at home or in a remote location is therefore possible.

The embodiments described herein are typically intended to facilitate separation, processing, and thermally controlled shipment of fluid samples in circumstances where prior art and conventional approaches are not available. In general, the embodiments described herein are intended to replace functions that would require large equipment that requires considerable power with a single apparatus of an embodiment.

Embodiments free of an external power source may be used in remote environments, at-home environments, emergency vehicles or other mobile applications. Prior art unpowered centrifuges, such as hand-crank operated spinners, do not provide the consistent spin rate and spin time performance required by regulations and standards for diagnostic testing. Further, balancing and operating a conventional centrifuge is not within the capability of most untrained users as may be common in remote or home environments. At-home or remote testing may be facilitated by a small, portable, powered centrifuge. Such a centrifuge will preferably have a minimal size to facilitate portability, fitting within a typical pocket, backpack, or purse. Emerging devices for higher capillary blood draw to obtain larger blood samples, such as the Tasso OnDemand product, which collects blood through a patch rather than a needle, may be available to users at home. Complete autonomous use by a user at home is therefore possible.

Embodiments described herein are typically intended to facilitate separation, processing, and thermally controlled shipment of fluid samples in circumstances where conventional approaches are not available. For instance, typical cold chain processing and shipment of a blood specimen typically requires use of a centrifuge and refrigerated ice packs. Such facilities are not available at every potential site of blood draw due to power requirement, space, untrained users, and time pressure. In general, the embodiments described herein are intended to replace functions that would typically require large equipment that requires considerable power.

Methods for processing and preserving biological samples with a combined apparatus are described. The devices may have built-in refrigeration capabilities, The devices may combine a simple self-balancing centrifuge device and an active, battery powered cooling apparatus, actively cooled PCMs, nr PCMs with a phase transition temperature above typical indoor ambient conditions.

DETAILED DESCRIPTION OF THE INVENTION

Embodiments of this invention overcome weaknesses of prior art. Examples, scenarios, drawings, descriptions, and embodiments are non-limiting.

The embodiments described herein typically include centrifugal devices intended to separate a heavy fraction from a light fraction in a fluid sample by rotation of a rotor at an effective spin rate. An example of such a fluid sample is a blood sample comprising plasma as the light fraction and blood cells as the heavy fraction. Such embodiments may also be used to separate serum from clotted whole blood. Some embodiments are intended to be used for applications where portability is required. Therefore, elements are included that minimize energy consumption and size. Further, embodiments disclosed are configured to separate a fluid sample contained in a single tube. Prior art and conventional centrifugal devices typically require rotor balancing by a trained individual. By including appropriate counterweights, embodiments do not require balancing by a user or a trained individual.

The embodiments described herein may include elements to provide thermal protection to a biological specimen for shipment. For example, an embodiment may be used to maintain a temperature range of between 2° C. to 8° C., between 15° C. to 30° C., between 11° C. to 32° C., between 15° C. to 8° C. and 32° C., below 0° C., and below −10° C., in a biological, regardless of external temperature and other conditions. Embodiments may be configured to provide thermal protection of samples for specific periods of time. For example, maximum time periods in the range of 12 to 36 hours, 24 to 72 hours, 24 hours or less, 48 hours or less, or one week or less. Elements in embodiments for this purpose may include insulation, passive cooling elements, or active cooling components. Insulation may include material with low thermal conductivity or reflective material with low emissivity. Such elements may be used in any combination.

Figure 1:
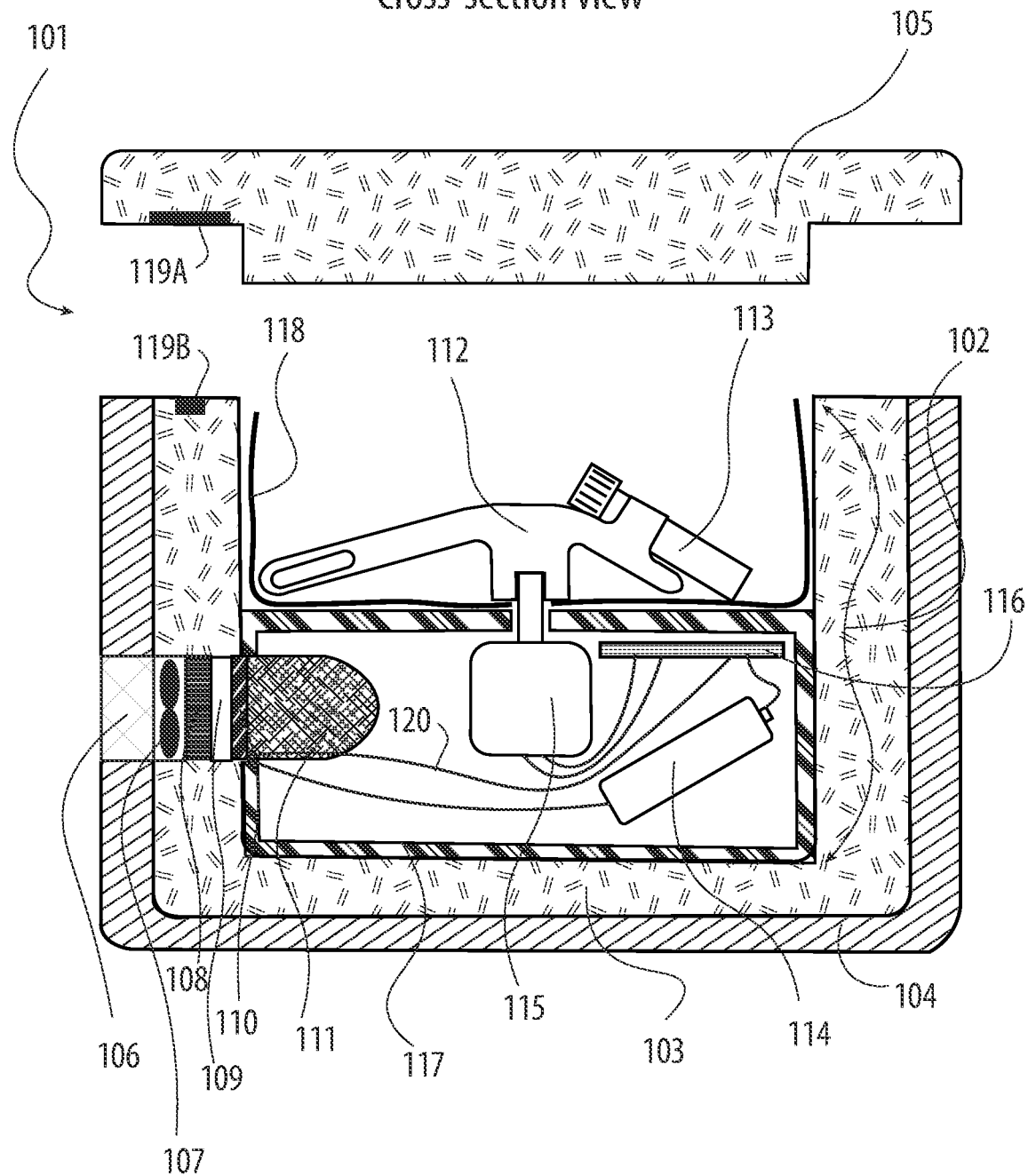
FIG. 1. Exemplary embodiment of a device for centrifugation and thermally regulated shipping.

Turning first to FIG. 1, an embodiment of blood or other sample separation and shipping apparatus 101 is shown in a cross sectional view. The apparatus 101, in one embodiment, comprises a centrifuge generally 102, insulating walls 103, outer package 104, insulating lid 105, vent for airflow 106, fan 107, thermo-electric cooler 108, air gap 109, phase change material 111, rotor 112, a tube 113, a battery 114, a motor 115, an electronic controller 116, a motor compartment 117, a safety liner 118, a lid sensor 119A and 119B, and wiring 120. The term centrifuge may be applied to the motor 115, controller 116, and rotor 112. The term may also include support structures such as container 117. The term may be applied minimally to the rotor 112. The insulating walls 103 and insulating lid 105 are for the purpose of maintaining a controlled temperature range for a biological sample, such as blood, in a tube 113 in a tube retainer as part of rotor assembly 112.

In particular, a purpose of the apparatus as a whole is to permit both centrifugal separation of a sample and temperature controlled shipping in a single, easy-to-use apparatus that does not require specialized training or external equipment, such as a power source or wireless controller. Free of user controls for spin speed and spin duration, untrained users such as a patient, a person at home, or at a remote medical clinic, may effectively use the apparatus, a substantial benefit not available in the prior art.

The insulating lid 105 and insulating walls 103 may comprise one or more insulating materials such as expanded polystyrene, vacuum panels, air bladders, reflective foils, or other known materials with low thermal conductivity and/or low emissivity. The insulating lid 105 may hermetically seal with the insulating wall 103. The outer package 104 may be made from cardboard, paperboard, plastic, a non-woven material such as polyethylene, or other packaging material. Alternately, the outer package 104 may be made from aluminum, steel, hard plastic, or other durable material to facilitate re-use.

In order to maintain the biological sample in the sample tube 113 within a desired temperature range, generally cooler than an ambient temperature, one or more active or passive thermal management elements are used. Such elements may connect with ambient air to remove heat. One embodiment uses an air channel 106 for this purpose. Elements, in any combination, as part of thermal management, include a fan 108, a thermo-electric cooler 108, air gap or heat conduction element 109, and a phase change material 111. An element with a high thermal mass, not shown, may also be used. The thermal management elements are shown thermally connected to the interior of the motor enclosure 117. However, thermal management elements may thermally connect with any elements inside of the thermal package comprising insulating walls 103 and insulating lid 105. A preferred embodiment uses only a phase change material 111 to avoid the need for penetration of the insulation 106 and electrical elements 108 and 109.

Continuing with FIG. 1, a rotor or rotor assembly 112 is shown in a simplified side view. The rotor 112 connects to a motor 115 via a motor shaft and rotor hub. The centrifuge 102 spins the biological sample in the tube 113 in a tube retainer as part of the rotor assembly 112. See figures following for more detail. Sample tube 113 is not part of preferred embodiments. In a typical method embodiment a use, such as a patient or care giver, places a biological sample such as a patient's blood, into tube 113 then places the tube into the tube retainer. A novel feature of embodiments and improvement over the prior art comprises a single tube retainer and pre-balanced rotor, to free a user from the need to balance the centrifuge.

Spinning may commence automatically when the insulating lid is placed on, in or over the insulating walls 103, as detected by a lid sensor 119A and 119B, operatively connected to an electronic controller 116 and power source, such as a battery 114. Effective spin speed and spin duration is controlled by the electronic controller 116. In a preferred embodiment, a spin speed and spin duration are predetermined. Electronic devices are interconnected with schematic wires, 120.

A safety liner 118 may be used to contain the sample in the sample tube 113 in the event of a failure, malfunction, or damage. A portion of the safety liner 118 is shown in FIG. 1. In use, the safety liner 118 would typically be fully closed. Closures may comprise adhesive, folding, zippers, plastic tongue and slot fasteners, hook and loop fasteners, ties, magnets, and the like, in any combination. A safety liner 118 may comprise gaskets or other seals. A safety liner may withstand an internal pressure of 95 kPA, such as to meet shipping requirements. A safety liner 118 may comprise absorbent, desiccant, or coagulating material.

A lid sensor is shown schematically as a pair of elements 119A and 199B. A lid sensor may comprise a ferric sensor, magnetic sensor, reflective sensor, hall effect sensor, accelerometer, light sensor, mechanical sensor, pressure sensor, electrical switch, and the like. Portion 119A may be a reflective strip, ferrous material, an electrically conducting material a magnet, a rigid element, a protrusion, and the like. Portion 119B is typically operatively connected to the electronic controller 116. More than one lid sensor may be used. The lid 105 should make a thermally secure fit with the wall insulation 103. This may be accomplished via a press fit, adhesive, barbs, mechanical clasps, elastic bands, gaskets, or other elements, in any combination.

The battery or power source 114 may comprise primary or rechargeable battery, or a super-cap for example. Suitable battery technologies include nickel-metal hydride, alkaline, or zinc chloride batteries. A battery 114 may be placed anywhere in or on the apparatus 101. An electronic controller 116 may comprise a temperature sensor, timer, shock sensor, temperature history record, or other sensors and data storage.

The apparatus 101 may include a thermal moderating material or phase change material 111, which may be in direct contact with a conductive block or may be in direct contact with one side of the thermoelectric cooler 108. In some embodiments, the thermal moderating material 111 may comprise a pouch containing a phase change material such as fatty acids, paraffin waxes, or aqueous solutions. Phase change material may be selected or configured to have a melting temperature within a relevant temperature range for shipping as discussed elsewhere herein. For example, coconut oil with a melting temperature range of 27-32 degrees Celsius may be used as a phase change material to maintain sample tube 113 at a temperature at or below 32 degrees Celsius. Alternately or in addition, a thermal moderating material with a high specific heat capacity. Another side of the thermoelectric element may be in contact with a heat sink. A fan 107 may exhaust warm air out of a vent 106.

A thermoelectric component, such as a thermoelectric cooler may be configured to freeze the phase change material, such that energy is later required to melt the phase change material. The rotor or rotor assembly 112 may be configured to counterbalance a single tube such than no active or manual balancing is required by a user. The motor may be encased or suspended in elastomeric material (not shown) to enable centrifugation of a moderately imbalanced tube.

An embodiment of FIG. 1 shows a thermoelectric cooling apparatus intended to ensure that a thermal modulating material is initially at a set temperature within an effective temperature range. For instance, the cooling apparatus may ensure that the temperature is below the melting temperature of a phase change material. The active cooling components such as the heat sink and thermoelectric element may be positioned differently than shown, such as at the top of the centrifuge. It should be understood that thermoelectric cooling requires exposure an exterior portion of the package so waste heat may be removed. Embodiments may employ active cooling only during sample processing by centrifugation in order to ensure the phase change material is frozen prior to shipment. In such embodiments, removal of waste heat may occur while the package is open rather than through a dedicated opening in the package. Alternately, cooling may occur throughout the shipping process. The circuit board may monitor temperature and report if a threshold temperature has been crossed during shipment. For instance, logic on the circuit board 116 may report whether a temperature of 32° C. was exceeded. The upper or lower end of any temperature range discussed herein, or an average temperature, may also be reported. Such reporting may be via an internal or external visible indicator such as an LED, LCD or a passive material such as a fuse temperature sensitive chemical. Such reporting may be via an audible alarm. Such reporting may be via a wireless interface, such as Bluetooth, Wi-Fi or cellular.

Embodiments may run a thermoelectric element to maintain a temperature range such as required to maintain living cells. For example, a temperature range of 35 to 39° C. may be maintained. Phase change material with a freezing point within the elevated temperature range may be employed to prolong maintenance of the desired temperature range in the absence of power.

A centrifugal portion and an active cooling portion of an apparatus may be configured to work as a combined unit. A battery may be used, directly or indirectly, to power the centrifugal motor and the active cooling apparatus. Logic on a circuit board may control both the centrifugal apparatus and the active cooling apparatus. The housing of the centrifugal device may comprise phase change material. The packaging or the housing of the centrifugal device may comprise vacuum insulation such as a Dewar flask. The package may be configured for sterilization and re-use for multiple shipments. Tubes discussed herein may be cylindrical or disk-shaped containers adapted to be rotated about an axis of rotation.

A method of preparing biological samples for shipment may include the following steps: (1) open the package centrifuge apparatus by removing or opening the lid or cover; (2) place blood or another sample inside a tube or other rotatable container; (3) place the tube in tube retainer in the rotor; (4) close the lid and optionally a liner; (5) initiate centrifugation, which may occur automatically by closing a package lid; (6) ship the complete apparatus. The method may explicitly be free of manual balancing, setting a timer, programming the centrifuge, verifying temperature, or pressing buttons. The cooling apparatus may be activated when the package centrifuge apparatus is opened, and continue cooling until the package lid is closed. Alternately, the cooling apparatus may be operative or activated while the centrifuge is spinning. The centrifuge may spin for a predetermined amount of time at an effective spin rate as preprogrammed in the circuit board after the package lid is closed. The predetermined spin time may be in a range between 2 and 30 minutes. Alternately, the defined spin time may be in a range between 4 and 15 minutes.

Considering now the thermal moderating material 111, it may comprise a phase change material. The phase change material may comprise water, an aqueous solution of hydrated salts, paraffins, vegetable oils, or blends of fatty acids, in any combination. Phase change materials may absorb a heat of fusion when transitioning from a solid phase to a liquid phase at a melting point temperature, thereby providing a means of stabilizing ambient temperature in the vicinity of the melting point temperature. The phase change material will be selected such that the melting point temperature of the phase change material is near the upper value of an intended temperature range for the sample tube. For example, a phase change material with a melting point temperature of 27° C. may be used to maintain an intended temperature range of 11° C. to 30° C. when the package is exposed to an elevated temperature of 35° C. or higher. The phase change material will typically comprise a solid or a liquid/solid blend within the intended temperature range and will typically comprise a liquid above the intended temperature range. If maintenance of an elevated temperature is desired, the phase change material may comprise a liquid or a liquid/solid blend within the intended temperature range and may comprise a solid below the intended temperature range. For example, a phase change material with a melting point temperature of 4° C. may be used to maintain an intended temperature range of 2° C. to 25° C. when the package is exposed to a temperature of −10° C. The apparatus may comprise a phase change material integrated within the insulation, thereby enabling solidification of the phase change material by placing the entire apparatus or a portion in a refrigerator for an effective time period. The effective time period may be a range of 30 minutes to 24 hours or preferably about 8 hours or overnight. More than one phase change material may be used. For example, a first phase change material may have a melting temperature of 4° C. and a second phase change material may have a melting temperature of 27° C., and together the first and second phase change materials will help maintain an intended temperature range of 2° C. to 30° C.

The phase change material may be integrated directly within a sealed chamber within the centrifuge housing. Alternately, the phase change material may be placed within a pouch or a bladder or a primary compartment. The phase change material may be reusable such that the package and the centrifuge may be refrigerated and shipped multiple times. The phase change material may occupy a volume of the centrifuge housing comprising more than one third of the total volume of the centrifuge housing. For example, the phase change material may occupy one half to three-quarters of the total volume of the centrifuge housing. The phase change material may occupy most of the volume of the centrifuge housing that is not occupied by other components. The electronic controller 116 may comprise a temperature sensor configured to monitor a temperature of the phase change material. The electronic controller may enable a first signal such as an LED or LED that provides an indication that a temperature of the phase change material is appropriate for shipping. For example, a green LED may be illuminated if the temperature of a phase change material with a 27° C. melting point temperature is below 27° C. Following shipping, the electronic controller may enable a second visual indicator that provides an indication that a temperature of the phase change material deviated or did not deviate from and intended temperature range. For example, a red LED may be illuminated if a temperature of the phase change material was measured to exceed 30° C., where the intended temperature range was 2° C. to 30° C. The second visual indicator may be triggered upon opening of the lid 105.

Figure 2A:
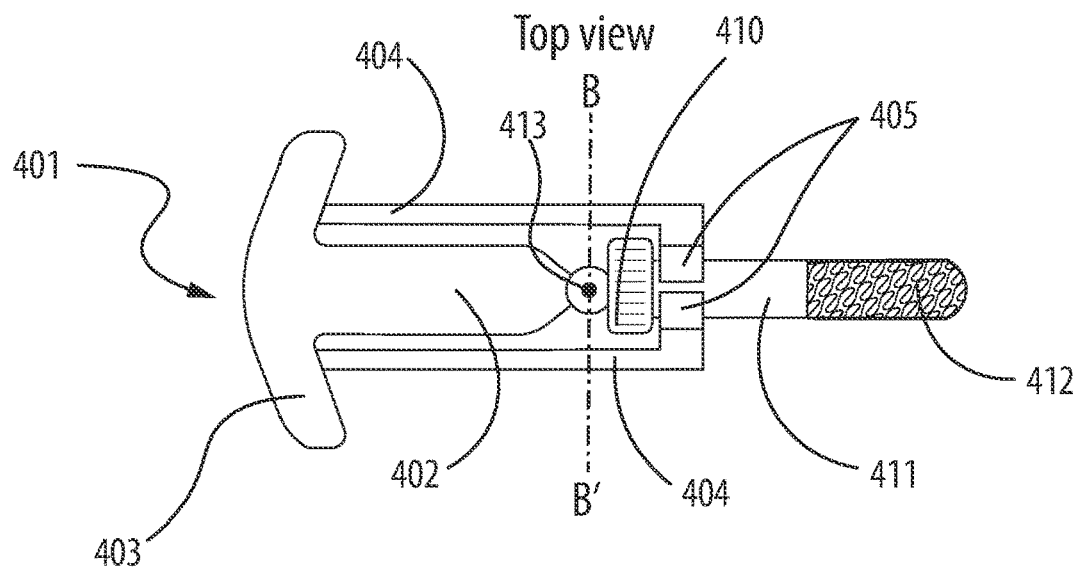
FIG. 2A. Exemplary top view of a rotor assembly.
Figure 2B:
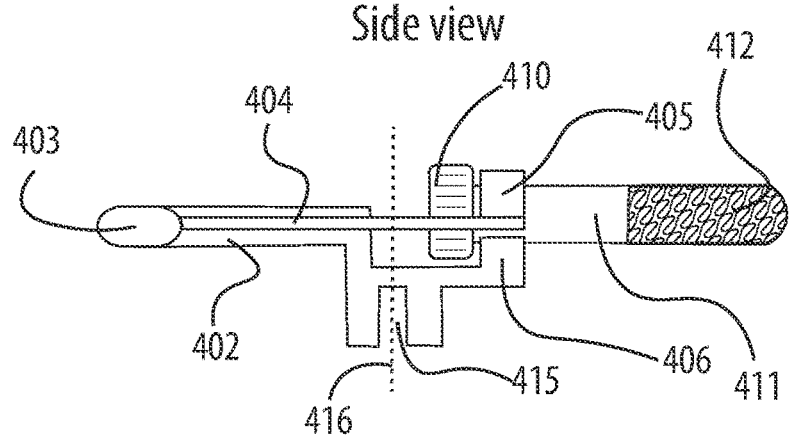
FIG. 2B. Exemplary side view of a rotor assembly.
Figure 2C:
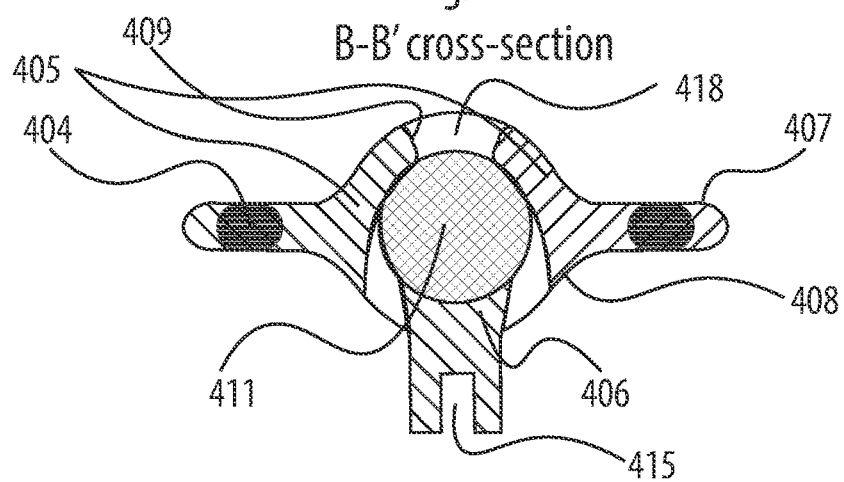
FIG. 2C. Exemplary cross-section of a rotor assembly.

FIG. 2A provides a top view embodiment of an unenclosed snap fit rotor 401 comprising a rotor body 402 and counterweight 403 that may reach out with arms 404 to hold a sample tube 411 by upper clasps 405. The sample tube 411 may be placed into the rotor 401 when pressed by hand into the upper clasps 405 through an opening 103. The rotor 401 may comprise rubber or other elastomeric materials for example, where the upper clasps 405 and lower clasps 406 contact the sample tube 411, to increase friction with the tube sample 411 and prevent it from shifting around during commencement or termination of centrifugation around the axis of rotation 416. In another embodiment, the rotor 401 may wrap around the sample tube lid 410 in order to prevent leakage of the fluid sample 412, in the case that the tube lid 410 were to detach, especially if the tube 411 were held in a horizontal position. The three views of a rotor or rotor assembly shown in FIGS. 4A, 4B and 4C is nominally in a horizonal plane, as can be seen in FIG. 4B. This is a distinctly different embodiment shape of a rotor or rotor assembly embodiment shown 112 in FIG. 1, where the ends of rotor 112 are bent downward around an axis of rotation.

FIG. 4B shows a side view of the rotor embodiment 401 so that the hub 415 and lower clasps 406 of FIG. 4A may also be seen. The upper clasps 405 and lower clasps 406 may together hold the sample tube 411 in a position opposite the counter weight(s) 403. The hub 415 may mate with a motor shaft of motor 115 device such that the motor centrifugally rotates or spins sample tube 411 around an axis of rotation 416.

FIG. 4C shows a schematic cross section of the rotor or rotor assembly 401 comprising lead surface 407 edges comprising an aerodynamic extension 408, and an entry surface 409. The entry surface 409 shows an opening or tube retainer where the sample tube 102 may be pressed into place between the two sides of the upper clasps 405 and lower clasps 406 within the rotor or rotor assembly 401. This way, a mid-section of the tube 102 is snap-fitted into the rotor 401 so that the tube lid 410 is behind the upper clasp 405 and lower clasp 406, and the bottom end of the sample tube 411 may be seen centrally. The arms 404 may have a lead surface 407 protruding outwards from the tube 102 as part of the aerodynamic extension 408. Aerodynamic design of the rotor or rotor assembly 401 with rounded, smooth edges may minimize wind resistance and vibration of the rotor 401 during spin.

Figure 3:
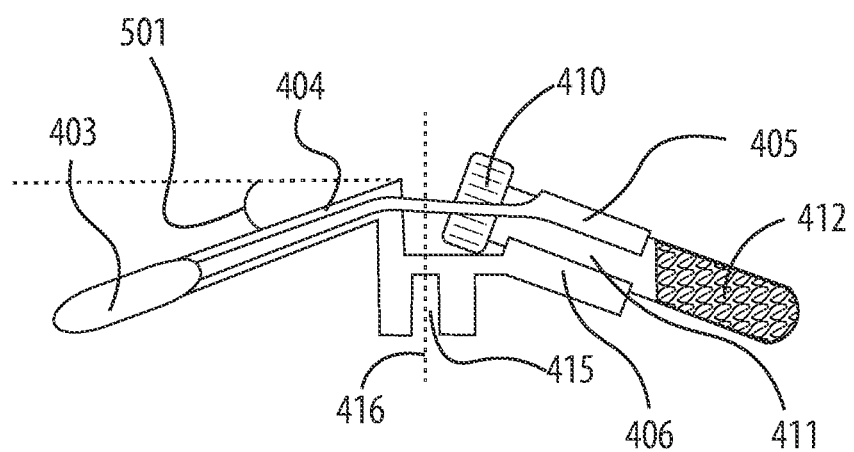
FIG. 3. Exemplary side view of a second embodiment of a rotor assembly.

Turning now FIG. 5, we see an embodiment of a rotor or rotor assembly, wherein the rotor may be angled 501 with respect to a horizontal plane normal to the axis of rotation 416, between 5 and 85 degrees, or preferably between 10 and 60 degrees. Otherwise similar components may comprise the rotor such as counter weight 403 that may reach out with arms 404 to hold the tube 411 with a tube lid 410 containing a fluid sample 412 by the upper clasps 405 and lower clasps 406 to mate at the hub 415 to rotate around the axis of rotation 416. This "angled" embodiment, as compared to a "straight" embodiment shown in FIGS. 4A, 4B and 4C, may decrease the overall diameter of the rotor such that a compact centrifugation system may be optimized, reducing the size, weight and cost. By tilting the tube 411, a smaller radius is swept by the tube, enabling a smaller footprint for a complete apparatus 101. Further, the fluid sample 412 may be less likely to leak if the tube lid 410 is removed, is damaged, or leaks. The "angled" rotor embodiment of FIG. 3 is shown schematically in FIG. 1 as 112.

We now describe additional details in some embodiments. Thermal moderating material 111 may comprise a phase change material. The phase change material may comprise water, an aqueous solution of hydrated salts, paraffins, vegetable oils, or blends of fatty acids. Phase change materials may absorb a heat of fusion when transitioning from a solid phase to a liquid phase at a melting point temperature, thereby providing a means of stabilizing ambient temperature in the vicinity of the melting point temperature. The phase change material will be selected such that the melting point temperature of the phase change material is near the upper value of an intended temperature range for the sample tube. For example, a phase change material with a melting point temperature of 27° C. may be used to maintain an intended temperature range of 11° C. to 30° C. when the apparatus 101 is exposed to an elevated temperature of 35° C. or higher. The phase change material will typically comprise a solid or a liquid/solid blend within the intended temperature range and will typically comprise a liquid above the intended temperature range. If maintenance of an elevated temperature is desired, the phase change material may comprise a liquid or a liquid/solid blend within the intended temperature range and may comprise a solid below the intended temperature range. For example, a phase change material with a melting point temperature of 4° C. may be used to maintain a desired temperature range of a sample of two ° C. to 25° C. when the package is exposed to an ambient temperature of −10° C. The apparatus may comprise a phase change material integrated within the centrifuge housing, thereby enabling solidification of the phase change material by placing the entire centrifuge or the entire package in a refrigeration device for an effective time period. The effective time period may be a range of 30 minutes to 24 hours or preferably about eight hours or overnight. More than one phase change material may be incorporated within the centrifuge housing. For example, a first phase change material may have a melting temperature of 4° C. and a second phase change material may have a melting temperature of 27° C., and together the first and second phase change materials will help maintain an intended temperature range of two ° C. to 30° C.

The phase change material may be integrated directly within a sealed chamber within the centrifuge housing. Alternately, the phase change material may be placed within a pouch or a bladder or a primary compartment. The phase change material may be reusable such that the package and the centrifuge may be refrigerated and shipped multiple times. The phase change material may occupy a volume of the centrifuge housing comprising more than one third of the total volume of the centrifuge housing. For example, the phase change material may occupy one half to three quarters of the total volume of the centrifuge housing. The phase change material may occupy most of the volume of the centrifuge housing that is not occupied by other components. The electronic controller may comprise a temperature sensor configured to monitor a temperature of the phase change material. The electronic controller may set a first visible indicator such as an LED that provides an indication that a temperature of the phase change material is appropriate for shipping. For example, a green LED may be illuminated if the temperature of a phase change material with a 27° C. melting point temperature is below 27° C. Following shipping, the electronic controller may set a second visible indicator that provides an indication that a temperature of the phase change material deviated from the intended temperature range. For example, a red LED may be illuminated if a temperature of the phase change material was measured to exceed 30° C., where the intended temperature range is 2° C. to 30° C. The second visible indicator light may be enabled upon opening of the package lid.

A compact apparatus or method of active thermal management, such as described in embodiments herein, may be useful for high value shipments that require end-to-end thermal regulation such as biological samples, even if they are shipped in large, refrigerating containers as part of a shipping journey, An embodiment of apparatus 101 may be less than 30 cm or less than 15 cm in length, width or height, in any combination. An embodiment of apparatus 101 may be less than 0.03 cubic meters in volume. An embodiment of apparatus 101 may be designed or configured for sanitizing or disinfecting by alcohol, bleach, radiation, ethylene oxide, appropriate aerosols, or other sanitizing or sterilizing means. An embodiment may be reusable. A motor may be configured to spin the rotor at an effective spin rate between 2,000 and 15,000 RPM.

In one embodiment, an apparatus is adapted to maintain a temperature of a sample tube in the range of one ° C. to 30° C. for a time period of 48 hours at a mean ambient temperature of 35° C. Other temperature ranges to maintain a temperature of a sample tube are the range of 11° C. to 30° C., 11° C. to 25° C., zero ° C. to eight ° C., one ° C. to four ° C., and less than zero ° C. These temperature ranges may apply to the sample tube, the sample itself, or both.

Ambient temperatures in applications and embodiments where a sample must be kept at or below a maximum temperature include minimums or mean temperatures of 30° C., 40° C. and 45° C. Ambient temperatures in applications and embodiments where a sample must be kept above freezing include minimums or mean temperatures of zero ° C. and −10° C.

Method claims may use any described embodiments of apparatus in any combination.

A nexus and novelty of embodiments include automatic operation such that devices and methods may be used by untrained users and in remote locations.

"Battery" includes batteries and battery packs, either echargeable or primary use, "Blood sample" may comprise, or may be, any biological sample suitable for centrifugation, "Electronic controller" may include one or more printed circuit boards or functional equivalents, such as electronic modules. Electronic controller or one or more electronic elements may be mounted external to some or all insulation to avoid placing heat from operation within the container.

"Fluid" should be construed broadly to include any sample that may be spun to achieve separation, such as slurries, aggregates and aerosols.

"PCM" is a phase change material or functional equivalent.

"Sample tube" or "tube" should be construed broadly to include any container that may contain a fluid and may be spun.

"Sample" typically means a biological sample, and is generally a fluid sample, at least prior to spinning. The term "biological" typically refers to a biological sample.

"Shipping" should be construed broadly to include movement and storage, and inspection.

Degrees Celsius is abbreviated ° C. RPM means revolutions per minute. Kilopascals is abbreviated kPa.

Descriptions, scenarios, examples and drawings are non-limiting embodiments. All references to "invention" refer to "embodiments."

Embodiments described herein are of a device intended for use in blood separation, and methods of using the device.

Drawings are not to scale. Drawings and elements in drawings are schematic only.

Ideal, Ideally, Optimum and Preferred—Use of the words, "ideal," "ideally," "optimum," "optimum," "should" and "preferred," when used in the context of describing this invention, refer specifically to a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

May, Could, Option, Mode, Alternative and Feature—Use of the words, "may," "could," "option," "optional," "mode," "alternative," "typical," "ideal," and "feature," when used in the context of describing this invention, refer specifically to various embodiments of this invention. Described benefits refer only to those embodiments that provide that benefit. All descriptions herein are non-limiting, as one trained in the art appreciates. The phrase, "configured to" also means, "adapted to." The phrase, "a configuration," means, "an embodiment."

All numerical ranges in the specification are non-limiting exemplary embodiments only.

Embodiments of this invention explicitly include all combinations and sub-combinations of all features, elements and limitations of all claims. Embodiments of this invention explicitly include all combinations and sub-combinations of all features, elements, examples, embodiments, tables, values, ranges, and drawings in the specification, Figures, drawings, and all drawing sheets. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substitution thereof to any and all other device claims, including all combinations of elements in device claims.

We claim:

1. An apparatus for blood sample separation and shipping comprising:
   (a) an outer container:
   (b) a thermal insulation layer within the outer container and defining a receiving area;
   (c) a centrifuge assembly within the receiving area of the thermal insulation layer, wherein the thermal insulation layer is between the centrifuge assembly and the outer container, the centrifuge assembly comprising:
   (d) a motor compartment;
   (e) a rotor assembly comprising a rotor body, a fixed counterweight, an attachment hub, and exactly one sample tube retainer;
   (f) a centrifuge motor adapted to spin the rotor assembly around an axis of rotation;
   (g) an electronic controller operatively connected to the centrifuge motor;
   (h) a battery, wherein the battery provides power to the centrifuge motor and to the electronic controller;
   (i) a safety liner surrounding at least a portion of the rotor assembly within the receiving area of the thermal insulation layer;
   (j) a thermally insulating lid comprising a thermal seal; and
   (k) one or more thermal management-elements.

2. The apparatus of claim 1 further comprising:
a lid sensor operatively connected to the electronic controller.

3. The apparatus of claim 1 wherein:
the apparatus is free of manually operated controls and is free of a manually adjustable counterweight.

4. The apparatus of claim 1 wherein:
the apparatus is free of manually operated buttons.

5. The apparatus of claim 1 wherein:
the apparatus is free of a manual control for spin time and free of a manual control for spin speed.

6. The apparatus of claim 1 wherein:
the apparatus is adapted to maintain a sample tube placed in the exactly one sample tube retainer at a temperature from 15° C. to 30° C. for a pre-determined time period.

7. The apparatus of claim 1 wherein:
the one or more thermal management elements comprises a phase-change material.

8. The apparatus of claim 1 wherein:
the one or more thermal management elements comprises a thermoelectric cooler.

9. The apparatus of claim 1 wherein:
the exactly one sample tube retainer is adapted to hold a sample tube at a fixed angle greater than 0 degrees and less than 20 degrees downward from a plane normal to the axis of rotation.

10. The apparatus of claim 1 wherein:
the electronic controller comprises an automatic timer that controls a spin time of the centrifuge motor in a predetermined time range of one minute to 120 minutes.

11. The apparatus of claim 1 wherein:
the safety liner is adapted to protect against leakage from a sample tube in the exactly one sample tube retainer.

12. The apparatus of claim 1 wherein:
the safety liner is adapted to protect against rupture of the safety liner during an internal pressure of 95 kPA or less inside the safety liner.

13. The apparatus of claim 1 wherein:
the rotor assembly is configured such that a center of mass of the rotor assembly is within two mm of the axis of rotation when a sample tube comprising a predetermined sample volume is in the exactly one sample tube retainer.

* * * * *